United States Patent [19]

Cohen

[11] 4,425,122

[45] Jan. 10, 1984

[54] PARENTERAL APPARATUS

[76] Inventor: Milton J. Cohen, 10823 Burbank Dr., Potomac, Md. 20854

[21] Appl. No.: 319,695

[22] Filed: Nov. 9, 1981

[51] Int. Cl.³ .............................................. A61M 5/00
[52] U.S. Cl. ................................................. 604/237
[58] Field of Search ................. 604/33, 34, 89, 90, 604/91, 236, 237, 238, 246, 249, 256, 411; 215/307; 251/342, 349, 356

[56] References Cited

U.S. PATENT DOCUMENTS

| | | | |
|---|---|---|---|
| 337,003 | 3/1886 | Luedemann | 215/307 |
| 1,143,855 | 6/1915 | Park | 215/307 |
| 1,712,070 | 5/1929 | Cressler | 604/237 |
| 2,642,064 | 6/1963 | Lawshe | 128/216 |
| 2,728,341 | 12/1955 | Roehr | 128/218 |
| 3,102,539 | 9/1963 | Goldberg | 128/218 |
| 3,308,809 | 3/1967 | Cohen | 604/237 |
| 3,380,449 | 4/1968 | Sarnoff | 128/218 |
| 3,391,695 | 7/1968 | Sarnoff | 128/218 |
| 3,401,693 | 9/1968 | Cohen | 128/221 |
| 3,424,155 | 1/1969 | Sarnoff | 128/218 |
| 3,459,177 | 8/1969 | Deuschle | 604/237 |
| 3,557,787 | 1/1971 | Cohen | 128/220 |
| 4,009,716 | 3/1977 | Cohen | 128/218 |
| 4,143,853 | 3/1979 | Abramson | 604/237 |

Primary Examiner—John D. Yasko
Attorney, Agent, or Firm—Blodgett & Blodgett

[57] ABSTRACT

A unitary closure and delivery means for dispensing solutions for parenteral administration from containers having an open end with a constricted neck, comprising an outwardly directed portion extending from the constricted neck and an inwardly directed portion held in inwardly displaceable, sealable relation within said constricted neck. The outwardly directed portion is channeled with an axially directed bore. The inwardly directed portion has at least one axial bisecting division which extends to and communicates with the bore. The opposing surfaces of the division are normally separated, but when mated by compressive engagement of the divided parts while held within the neck form a liquid impermeable seal. When the unit is urged inwardly from the neck into the body of the container, the surfaces of the bisecting division separate to form a patent path of communication with the interior of the container and its contents.

8 Claims, 4 Drawing Figures

FIG. 1
FIG. 2
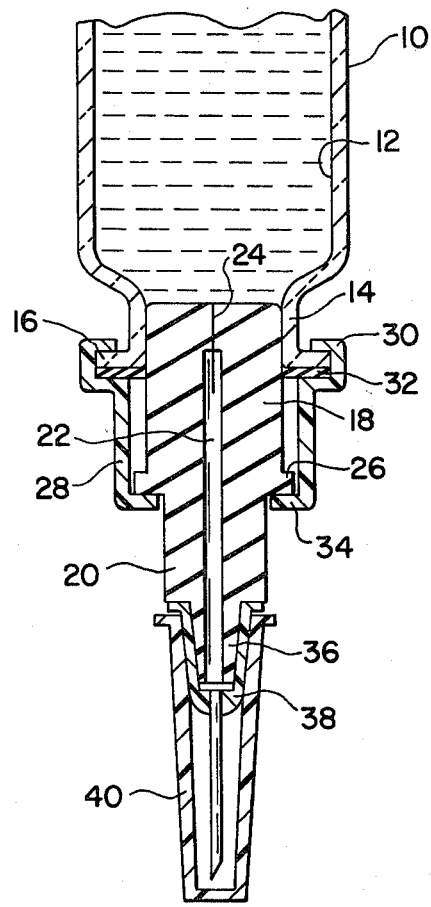
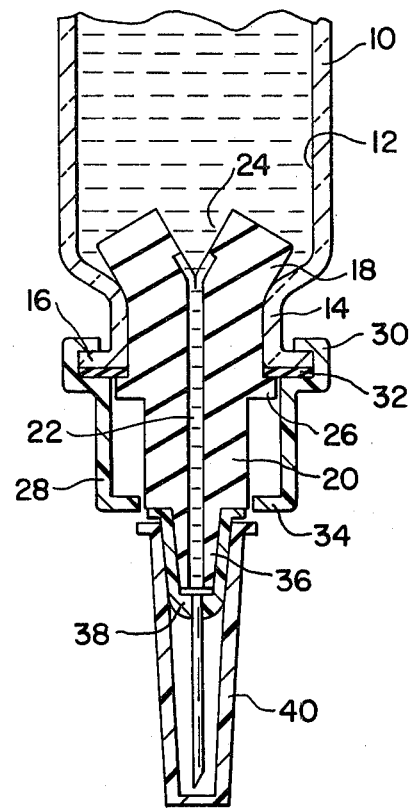

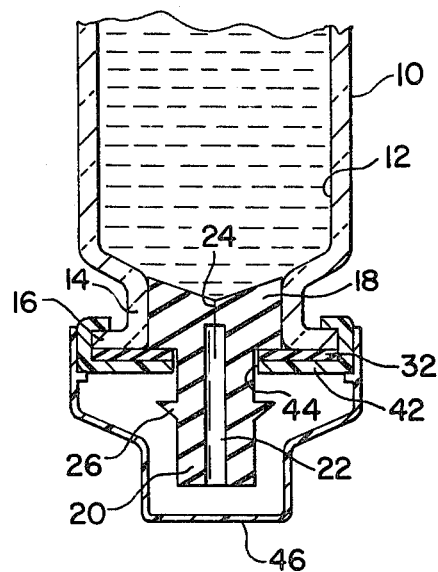
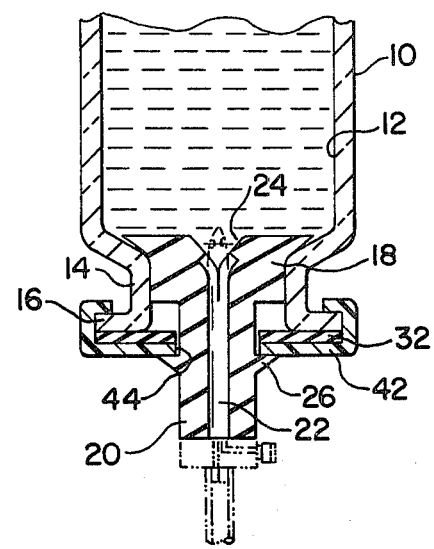

PARENTERAL APPARATUS

BACKGROUND OF THE INVENTION

The present invention relates to single use containers for dispensing prefilled solutions for parenteral administration, and more particularly to a unitary closure and delivery means applicable to such containers.

A prefilled disposable hypodermic syringe, for example, in which the contents are stored in a sealed, sterile condition, and out of contact with the needle or other administration means, commonly comprises a rigid tubular cartridge of glass or other suitable material having a discharge end constricted to form a neck of reduced diameter with an annular lip. The discharge opening is usually sealed with a penetrable closure, and the device is further provided with a hypodermic needle pointed at both ends, or has other closure-piercing means mounted in a spaced relationship with the penetrable closure to prevent contact of the needle with the contents until time of use. In practice, the penetrable closure may be pierced by relative movement of the closure-piercing means and the cartridge so that the closure is penetrated and communication with the contents is established. This type of construction is described in the following summary representative of the prior art.

DESCRIPTION OF THE PRIOR ART

Roehr, U.S. Pat. No. 2,728,341, Sarnoff, U.S. Pat. Nos. 3,380,449, 3,391,695, and 3,424,155, and my 3,401,693, 3,557,787, and 4,009,716, are representative of current prefilled injectors in which the contents are stored out of contact with the needle or other administration means. These are generally sealed with penetrable closures having piercing means in spaced relationship and means for effecting relative movement to cause penetration or rupture of the closure. Lawshe, U.S. Pat. No. 2,642,064, provides a perforable diaphragm integral with the container, but again in spaced relationship for relative piercing movement.

Such constructions generally necessitate assembly of a multiplicity of precision parts prior to mounting on the syringe body, and usually require an integrally mounted needle of pre-selected length and gauge, or specially fabricated piercing means.

Closures for containers of injectable materials in which the contents are sealed from the needle or injection means but in which piercing or rupture of the closure is not required are exemplified in Park, U.S. Pat. No. 1,143,855, which describes a stopper with a needle-receiving aperture extending therethrough, and the aperture being closed by a temporary closing device of greater diameter held within the aperture and adapted to be forced out of the aperture by the shank of the needle when passed therethrough. Goldberg, U.S. Pat. No. 3,102,539, similarly teaches a closure with a traversing center bore and an ejectable seal member closing the bore combined with means for containing the ejected seal member to prevent blocking of the administration needle.

This type of construction also requires precision assembly, and in use could be subject to malfunction or difficulty in activation.

Stopper constructions having a longitudinal central passage interconnected with upright incisions are found in the prior art, as are tubular stoppers with tapers or frustoconical configurations.

In U.S. Pat. No. 337,003, Luedemann taught a bottle-stopper made of wood or equivalent substance having a longitudinal central passage and upright incisions or slots in its body forming the lower part into laterally movable sections, and a passage between the sections in alignment with the bore. The invention consisted in making the tubular stopper elastic at the lower part so that the sections could be crowded nearer together or forced a little farther apart to permit insertion into the neck of a bottle past an inwardly projecting shoulder which, by interaction with a peripheral groove, locked the stopper into the bottle. This construction permitted the contents to be dispensed through the passage, but prevented removal of the stopper and refilling the bottle.

Frustoconical shapes or tapers on stoppers or closures (where taught) are for the purpose of assuring a tight seal with the neck or walls of the container, or for making it difficult to remove the stopper once it was inserted.

Either a separate sealing means or separate means for accessing the contents of the container are required in these constructions.

SUMMARY OF THE INVENTION

Among objectives of this invention is to provide a closure and delivery means for a cartridge-type syringe body, and also applicable to other containers for solutions for parenteral administration, which is of simple construction, necessitates no intricate assembly, requires no seal-piercing means, with attendant problems of coring and introduction of particulates to the solutions, and allows the user the option of a standard needle of his choice, a plastic spike, transfer unit, or other configuration of administration means selected in accordance with preference or the dictates of use.

Other objectives of the invention and the ways in which such objectives are accomplished will become apparent from the following description of the invention taken in conjunction with the accompanying drawings of the embodiments:

FIG. 1 is a vertical sectional view through the axis of the discharge end of a vessel or container, such as a hypodermic syringe body, or the mouth of a serum vial or bottle, illustrating an embodiment of the invention in which the components are in a sealed condition.

FIG. 2 is a vertical sectional view of the container shown in FIG. 1, in which the components are in position for delivery of the contents.

FIG. 3 is a vertical sectional view showing another configuration of an embodiment of the invention applied to a container, with the components in a sealed attitude.

FIG. 4 is a vertical sectional view illustrating the vessel of FIG. 3, with the components in position for delivery of the contents.

DESCRIPTION OF THE PREFERRED EMBODIMENT

Referring to the drawings, the reference numeral 10 designates generally the discharge end portion of a glass or plastic cartridge-type syringe body. Those skilled in the art will recognize that this conformation is also essentially representative of the open end of the type of serum vial or bottle commonly used for commercial packaging of small volume parenteral solutions, and of some bottles for large volume parenteral solutions, and that in the descriptions of the practice of the invention, the reference numerals may apply to the open end of a syring cartridge, a vial, or other container with a similar structure as well.

FIG. 1 illustrates a container 10 having an open end with a constricted neck 14 and an annular lip 16, and a unitary closure and delivery means, such as the member 18 of essentially cylindrical configuration, molded or otherwise fashioned from a resilient, compressible material such as rubber, having an outwardly directed main body portion 20 extending from the constricted neck 14, and an inwardly-directed portion 18 sealably engaging the inner surface of the neck but slideable therein with the application of nominal force in the axial direction. The outwardly directed portion 20 is channeled with an axially directed passage or bore 22 which communicates with at least one axially bisecting division 24 at the inwardly-directed end. The opposing surfaces formed by said bisecting division are normally separated, but when mated by compressive engagement of the divided parts, as when held within the neck, form a liquid impermeable seal. Spaced between the ends of the member is an annular flange or projection 26 having a radial dimension greater than the radial dimension of the container neck opening 14, but less than the radial dimension of the lip 16. A cup-shaped retainer or fixture 28, having a skirt, 30 is secured to the container by crimping of said skirt around the lip 16 with the aid of an annular washer 32 fabricated from a resilient, compressible material, such as rubber. The body of said cup-shaped fixture 28 terminates in an internal annular shelf 34. The outwardly-directed end 20 of the member forward of the annular projection 26 protrudes slide-ably outward of said shelf 34, with the outwardly-facing surface of the annular projection 26 in contact with the inner surface of said shelf, and limiting outward and lateral motion of said member. Said forwardly protruding end is depicted as terminating in an integrally formed Luer taper 36 to which a hypodermic needle with a Luer hub 38, and protected by a suitable cover 40, has been separately attached.

In FIG. 2, nominal force has been applied inwardly to the member in the axial direction, such as by inward pressure on the needle cover 40, causing the inwardly-directed portion 18 to be displaced from the constricted neck 14 into the body 12 of the container. This inward displacement allowes the opposing surfaces of the axially bisecting division 24 at the inwardly-directed end to open to their normally separated condition, accessing the bore and establishing a patent path of communication with the interior of the container. Further movement of the member in the inward direction has been arrested by contact of the annular projection 26 with the lip 16.

In the modification shown in FIGS. 3 and 4, the inwardly-directed portion 18 of the member is restricted in outward motion by a so-called inner cap seal 42, commonly used in closure assemblies for serum vials and cartridges, in the form of a hollow cylindrical element which terminates in an outer end wall having a central opening 44 of smaller dimension than the constricted neck 14 and which is secured to the container by crimping of the inner end portion around the lip 16 with the aid of an annular washer 32 of a resilient, compressible material. The outwardly-directed portion 20 of the member has a radial dimension less than that of the central opening 44 of the cap seal and protrudes therefrom. Relative dimensions of the protruding end and the opening are such as to permit sliding passage of the protruding end through the opening. The annular projection 26, which may also be formed as a series of individual projections disposed radially, having a radial dimension greater than the opening, is spaced between the ends of the member outward of the cap to limit inward displacement of the member, when an inward force is applied, only to that required to permit opening of the opposing surfaces of the axially bisecting division 24 to their unstressed separated condition and access to the bore 22 for delivery of the contents of the container. The outer directed end of the member can be maintained in a sterile condition prior to use by a suitable protective cover 46, which can be dimensioned to conform to the desired configuration of the delivery means. FIGS. 3 and 4 depict a configuration suitable for delivery of an intravenous drip solution from a large volume parenteral solution bottle.

It will be apparent from the foregoing that changes may be made in details of construction, configuration, and applications without departing from the spirit of the invention as defined in the following claims.

I claim:

1. In a container for dispensing solutions for parenteral administration having an open end with a constricted neck, a unitary closure and delivery means, fashioned from a resilient, compressible material, comprising an outwardly directed portion extending from the constricted neck, and an inwardly directed portion held in inwardly displaceable sealable relation within said constricted neck, said outwardly directed and extending portion being channeled with an axially directed bore, and said inwardly directed portion being closed by compression of at least one axial bisecting division extending to and communicating with the bore, the opposing surfaces of said bisecting division being normally separated but which, when mated by compressive engagement of the divided parts while held within the neck, form a liquid-impermeable seal, and which, when the member is urged inwardly from the neck into the body of the container, separate to form a patent path of communication with the interior of the container and its contents.

2. A unitary closure and delivery means as claimed in claim 1, further comprising means for limiting inward and outward displacement of the unitary member.

3. A unitary closure and delivery means as claimed in claim 2, wherein said means for limiting inward and outward displacement of the unitary member comprises an annular projection spaced between the ends of the member interacting with a retaining means secured to the container.

4. A unitary closure and delivery means as claimed in claim 2, wherein the constricted neck of the container has an annular lip to which said retaining means is secured.

5. Parenteral appartus for use with a container 10 having a neck 14 with a bore, comprising:
(a) a unitary closure and delivery member formed of elastomer material and capable of axial movement in the bore from an outer sealing position to an inner open position,
the said member being formed in bifurcated form so that in unstressed condition it has a cylindrical main body 20 having a central passage 22 and two arms extending at a substantial angle to the main body, so that when the member is in the outer sealing position, the arms are pressed together to close off the central passage and so that, when the member is moved to the inner open position, the arms are in unstressed condition to expose the inner end of the central passage.

6. Parenteral apparatus as recited in claim 5, wherein the member is formed in the unstressed condition with a cylindrical main body and semi-cylindrical arms at one end, the arms having facing plane surfaces extending at acute angles to the axis of the main body, the portion of each plane surface adjacent the main body being formed with a groove connected to the central passage, but the remainder of each said plane surface being free of such a groove.

7. Parenteral apparatus as recited in claim 5, wherein a retainer 28 is mounted on the container to limit the axial movement of the member, and wherein the main body of the member is provided with a flange 26 which cooperates with the retainer to limit the axial movement.

8. Parenteral apparatus as recited in claim 7, wherein the neck of the container has a radial lip 16 which holds the retainer and which cooperates with the flange on the main body of the member to defne the inner open position of the member.

* * * * *